(12) United States Patent
Khait et al.

(10) Patent No.: US 7,833,151 B2
(45) Date of Patent: Nov. 16, 2010

(54) IN VIVO IMAGING DEVICE WITH TWO IMAGERS

(75) Inventors: Semion Khait, Tiberias (IL); Zvika Gilad, Haifa (IL)

(73) Assignee: Given Imaging Ltd., Yoqneam Ilite (IL)

( * ) Notice: Subject to any disclaimer, the term of this patent is extended or adjusted under 35 U.S.C. 154(b) by 1458 days.

(21) Appl. No.: 11/094,253

(22) Filed: Mar. 31, 2005

(65) Prior Publication Data

US 2005/0171398 A1 Aug. 4, 2005

Related U.S. Application Data

(63) Continuation-in-part of application No. PCT/IL03/01105, filed on Dec. 25, 2003.

(60) Provisional application No. 60/436,004, filed on Dec. 26, 2002.

(51) Int. Cl.
A61B 1/00 (2006.01)
A61B 1/04 (2006.01)

(52) U.S. Cl. .................... 600/109; 600/160

(58) Field of Classification Search .............. 600/109, 600/160, 302; 128/899; 348/76
See application file for complete search history.

(56) References Cited

U.S. PATENT DOCUMENTS

| | | | |
|---|---|---|---|
| 3,322,374 A | 5/1967 | King, Jr. | |
| 3,509,270 A | 4/1970 | Yorgensen et al. | |
| 3,616,532 A | 11/1971 | Beck | |
| 3,971,362 A | 7/1976 | Pope et al. | |
| 4,087,960 A | 5/1978 | Koichi | |
| 4,239,040 A | 12/1980 | Hosoya et al. | |
| 4,246,792 A | 1/1981 | Matzuk | |
| 4,278,077 A | 7/1981 | Mizumoto | |
| 4,431,005 A | 2/1984 | McCormick | |
| 4,439,197 A | 3/1984 | Honda et al. | |
| 4,447,677 A | 5/1984 | Miyahra et al. | |
| 4,628,150 A | 12/1986 | Luc | |
| 4,646,724 A | 3/1987 | Sato et al. | |
| 4,668,884 A | 5/1987 | Amao et al. | |
| 4,689,621 A | 8/1987 | Kleinberg | |
| 4,741,327 A | 5/1988 | Yabe | |
| 4,742,183 A | 5/1988 | Soloway et al. | |

(Continued)

FOREIGN PATENT DOCUMENTS

DE 3 440 177 6/1989

(Continued)

OTHER PUBLICATIONS

Office Action for U.S. Appl. No. 10/481,126 dated Feb. 24, 2006.

(Continued)

*Primary Examiner*—John P Leubecker
(74) *Attorney, Agent, or Firm*—Pearl Cohen Zedek Latzer, LLP

(57) ABSTRACT

A substantially spherical in vivo imaging device may be used for imaging body lumens in the GI tract. The imaging device may include for example a ballast weight for setting a preferred orientation of the device within the body lumen. The substantially spherical shape of the in vivo imaging device may facilitate capturing steady streams of imaging data in large body lumens. A method of manufacture is presented.

15 Claims, 8 Drawing Sheets

U.S. PATENT DOCUMENTS

| | | | |
|---|---|---|---|
| 4,742,817 A | 5/1988 | Kawashima et al. | |
| 4,803,992 A | 2/1989 | Lemelson | |
| 4,812,726 A | 3/1989 | Benii et al. | |
| 4,819,620 A | 4/1989 | Okutsu | |
| 4,844,076 A | 7/1989 | Lesho et al. | |
| 4,936,823 A | 6/1990 | Colvin et al. | |
| 4,939,792 A | 7/1990 | Urbish et al. | |
| 5,025,704 A | 6/1991 | Davis | |
| 5,187,572 A | 2/1993 | Nakamura et al. | |
| 5,217,449 A | 6/1993 | Yuda et al. | |
| 5,250,371 A | 10/1993 | Kleinert et al. | |
| 5,267,033 A | 11/1993 | Hoshino | |
| 5,279,607 A | 1/1994 | Schentag et al. | |
| 5,330,427 A | 7/1994 | Weissenburger | |
| 5,368,027 A | 11/1994 | Lubbers et al. | |
| 5,395,366 A | 3/1995 | D'Andrea et al. | |
| 5,398,670 A | 3/1995 | Ortiz et al. | |
| 5,398,689 A | 3/1995 | Connor et al. | |
| 5,415,181 A | 5/1995 | Hogrefe et al. | |
| 5,426,263 A | 6/1995 | Potter et al. | |
| 5,434,362 A | 7/1995 | Klosowiak et al. | |
| 5,448,511 A | 9/1995 | Paurus et al. | |
| 5,454,366 A | 10/1995 | Ito et al. | |
| 5,472,804 A | 12/1995 | Austin et al. | |
| 5,495,114 A | 2/1996 | Adair | |
| 5,508,781 A | 4/1996 | Imai et al. | |
| 5,558,640 A | 9/1996 | Pfeiler et al. | |
| 5,604,531 A | 2/1997 | Iddan et al. | |
| 5,643,175 A | 7/1997 | Adair | |
| 5,679,216 A | 10/1997 | Takayama et al. | |
| 5,681,260 A | 10/1997 | Ueda et al. | |
| 5,697,377 A | 12/1997 | Wittkampf | |
| 5,697,384 A | 12/1997 | Miyawaki et al. | |
| 5,725,474 A | 3/1998 | Yasui et al. | |
| 5,747,996 A | 5/1998 | Fuchs | |
| 5,819,736 A | 10/1998 | Avny et al. | |
| 5,833,603 A | 11/1998 | Kovacs et al. | |
| 5,929,901 A | 7/1999 | Adair et al. | |
| 5,984,875 A | 11/1999 | Brune | |
| 5,986,693 A | 11/1999 | Adair et al. | |
| 5,993,378 A | 11/1999 | Lemelson | |
| 6,043,839 A | 3/2000 | Adair et al. | |
| 6,099,482 A | 8/2000 | Brune et al. | |
| 6,121,922 A | 9/2000 | Mohan | |
| 6,149,581 A | 11/2000 | Klingenstein | |
| 6,188,355 B1 | 2/2001 | Gilboa | |
| 6,208,698 B1 | 3/2001 | Marchesani et al. | |
| 6,233,476 B1 | 5/2001 | Stommer et al. | |
| 6,240,312 B1 | 5/2001 | Alfano et al. | |
| 6,304,769 B1 | 10/2001 | Arenson et al. | |
| 6,313,456 B1 | 11/2001 | Miyashita et al. | |
| 6,324,418 B1 | 11/2001 | Crowley et al. | |
| 6,338,347 B1 | 1/2002 | Chung et al. | |
| 6,371,927 B1 | 4/2002 | Brune et al. | |
| 6,417,885 B1 | 7/2002 | Suzukie et al. | |
| 6,428,469 B1 | 8/2002 | Iddan et al. | |
| 6,547,723 B1 | 4/2003 | Ouchi | |
| 6,692,430 B2 | 2/2004 | Adler | |
| 6,709,387 B1 | 3/2004 | Glukhovsky et al. | |
| 6,711,423 B2 * | 3/2004 | Colvin, Jr. | 600/317 |
| 6,800,060 B2 | 10/2004 | Marshall | |
| 6,939,292 B2 * | 9/2005 | Mizuno | 600/118 |
| 6,944,031 B2 | 9/2005 | Takami et al. | |
| 6,951,536 B2 * | 10/2005 | Yokoi et al. | 600/128 |
| 7,044,908 B1 | 5/2006 | Montalbo et al. | |
| 2001/0006252 A1 | 7/2001 | Kim et al. | |
| 2001/0035902 A1 | 11/2001 | Iddan et al. | |
| 2001/0051766 A1 | 12/2001 | Gazdzinski | |
| 2002/0032366 A1 | 3/2002 | Iddan et al. | |
| 2002/0103417 A1 | 8/2002 | Gazdzinski | |
| 2002/0109774 A1 | 8/2002 | Meron et al. | |
| 2002/0143239 A1 | 10/2002 | Henzler et al. | |
| 2002/0146368 A1 | 10/2002 | Meron et al. | |
| 2002/0158976 A1 | 10/2002 | Vni et al. | |
| 2002/0165592 A1 | 11/2002 | Glukhovsky et al. | |
| 2002/0173718 A1 | 11/2002 | Frisch et al. | |
| 2002/0177779 A1 | 11/2002 | Adler et al. | |
| 2002/0198439 A1 | 12/2002 | Mizuno | |
| 2003/0013370 A1 | 1/2003 | Glukhovsky | |
| 2003/0018280 A1 | 1/2003 | Lewkowicz et al. | |
| 2003/0028078 A1 | 2/2003 | Glukhovsky | |
| 2003/0043263 A1 | 3/2003 | Glukhovsky et al. | |
| 2003/0045790 A1 | 3/2003 | Lewkowicz et al. | |
| 2003/0060734 A1 | 3/2003 | Yokoi et al. | |
| 2003/0085994 A1 | 5/2003 | Fujita et al. | |
| 2003/0114742 A1 | 6/2003 | Lewkowicz et al. | |
| 2003/0117491 A1 | 6/2003 | Avni et al. | |
| 2003/0167000 A1 | 9/2003 | Mullick et al. | |
| 2003/0171652 A1 | 9/2003 | Yokoi et al. | |
| 2003/0195415 A1 | 10/2003 | Iddan | |
| 2003/0208107 A1 | 11/2003 | Refael | |
| 2003/0214579 A1 | 11/2003 | Iddan | |
| 2003/0214580 A1 | 11/2003 | Iddan | |
| 2003/0216622 A1 | 11/2003 | Meron et al. | |
| 2004/0027459 A1 | 2/2004 | Segawa et al. | |
| 2004/0073087 A1 | 4/2004 | Glukhovsky et al. | |
| 2004/0087832 A1 | 5/2004 | Glukhovsky et al. | |
| 2004/0106849 A1 | 6/2004 | Cho et al. | |
| 2004/0171914 A1 | 9/2004 | Avni | |
| 2004/0215059 A1 | 10/2004 | Homan et al. | |
| 2004/0225189 A1 | 11/2004 | Kimoto et al. | |
| 2004/0225190 A1 | 11/2004 | Kimoto et al. | |
| 2004/0236182 A1 | 11/2004 | Iddan et al. | |
| 2004/0254455 A1 | 12/2004 | Iddan | |
| 2005/0025368 A1 | 2/2005 | Glukhovsky | |
| 2005/0043586 A1 | 2/2005 | Suzushima et al. | |
| 2005/0043587 A1 | 2/2005 | Fujimori et al. | |
| 2005/0049461 A1 | 3/2005 | Honda et al. | |
| 2005/0068416 A1 | 3/2005 | Glukhovsky et al. | |
| 2005/0075559 A1 * | 4/2005 | Houzego et al. | 600/424 |
| 2005/0124858 A1 | 6/2005 | Matsuzawa et al. | |
| 2005/0270169 A1 | 12/2005 | Drader et al. | |
| 2006/0004256 A1 * | 1/2006 | Gilad et al. | 600/160 |
| 2006/0015013 A1 | 1/2006 | Gilad et al. | |
| 2006/0264709 A1 | 11/2006 | Fujimori et al. | |

FOREIGN PATENT DOCUMENTS

| | | |
|---|---|---|
| FR | 2362556 | 8/1976 |
| FR | 2 688 997 | 10/1993 |
| IL | 143259 | 5/2001 |
| JP | 4144533 | 5/1992 |
| JP | 5015515 | 1/1993 |
| JP | 1994 6-114037 | 4/1994 |
| JP | 6114037 | 4/1994 |
| JP | 6114064 | 4/1994 |
| JP | 6154191 | 6/1994 |
| JP | 6285044 | 10/1994 |
| JP | 7111985 | 5/1995 |
| JP | 2000342522 | 12/2000 |
| JP | 2001-091860 | 4/2001 |
| JP | 2001091860 | 4/2001 |
| JP | 2001095755 | 4/2001 |
| JP | 2001095756 | 4/2001 |
| JP | 2001104241 | 4/2001 |
| JP | 2001104242 | 4/2001 |
| JP | 2001104243 | 4/2001 |
| JP | 2001104244 | 4/2001 |
| JP | 2001104287 | 4/2001 |
| JP | 2001112709 | 4/2001 |
| JP | 2001112710 | 4/2001 |
| JP | 2001112740 | 4/2001 |
| JP | 2001137182 | 5/2001 |
| JP | 2001231744 | 8/2001 |

| | | |
|---|---|---|
| JP | 2001245844 | 9/2001 |
| JP | 2002000556 | 1/2002 |
| JP | 2000342524 | 6/2002 |
| JP | 2000342525 | 6/2002 |
| JP | 2006-141897 | 6/2006 |
| WO | WO 00/10456 | 3/2000 |
| WO | WO 01/06917 | 2/2001 |
| WO | WO 01/08548 | 2/2001 |
| WO | WO 01/50941 | 7/2001 |
| WO | WO 01/69212 | 9/2001 |
| WO | WO 02/055126 | 7/2002 |
| WO | WO 02/094337 | 11/2002 |
| WO | WO 02/102224 | 12/2002 |
| WO | WO 03/003706 | 1/2003 |
| WO | WO 03/011103 | 2/2003 |
| WO | WO 2004/028336 | 4/2004 |
| WO | WO 2004/035106 | 4/2004 |
| WO | WO 2004/036803 | 4/2004 |
| WO | WO 2004/059568 | 7/2004 |
| WO | WO 2004/088448 | 10/2004 |

OTHER PUBLICATIONS

Final Office Action for U.S. Appl. No. 10/481,126 dated Oct. 10, 2006.
Office Action for U.S. Appl. No. 10/481,126 dated Mar. 29, 2007.
Office Action for U.S. Appl. No. 10/481,126 dated Sep. 19, 2007.
Final Office Action for U.S. Appl. No. 10/481,126 dated Jul. 23, 2008.
Office Action for U.S. Appl. No. 10/481,126 dated Jan. 21, 2009.
Office Action for U.S. Appl. No. 10/046,541 dated Oct. 20, 2004.
Final Office Action for U.S. Appl. No. 10/046,541 dated May 19, 2005.
Office Action for U.S. Appl. No. 10/046,541 dated Jan. 12, 2006.
Final Office Action for U.S. Appl. No. 10/046,541 dated Jun. 15, 2007.
Office Action for U.S. Appl. No. 10/046,541 dated Aug. 8, 2007.
Office Action for U.S. Appl. No. 10/046,541 dated May 19, 2008.
International Search Report of Application No. PCT/IL02/00042, dated Sep. 18, 2002.
Written Opinion of Application No. PCT/IL02/00042, dated May 19, 2003.
Office Action of U.S. Appl. No. 10/046,541 mailed on Feb. 17, 2009.
U.S. Appl. No. 09/807,892, filed Jun. 6, 2001, Meron et al.
U.S. Appl. No. 10/200,548, filed Jul. 23, 2002, Glukhovsky et al.
U.S. Appl. No. 10/724,109, filed Dec. 1, 2003, Glukhovsky et al.
U.S. Appl. No. 10/166,025, filed Jun. 11, 2002, Lewkowicz et al.
U.S. Appl. No. 10/213,345, filed Aug. 7, 2002, Glukhovsky.
U.S. Appl. No. 10/493,751, filed Apr. 27, 2004, Glukhovsky et al.
The Heidelburg pH Capsule System Telemetric Fasting Gastric Analysis, Heidelburg international. incorporated.
Heidelberger Kapsel—ein Kleinstsender fur die pH-Messung im Magen, Lange, et al., Telefunken-Zeitung, Jg 36 (1963) Heft 5, pp. 265-270.
New Smart Plastic Has Good Memory—Turke, European Medical Device Manufacturer, devicelink.com.
Robots for the Future—Shin-ichi, et al. http://jin.jcic.or.jp/nipponaia13/sp05 html.
The Radio Pill, Rowlands, et al., British Communications and Electronics, Aug. 1960, pp. 598-601.
Video Camera to "TAKE"—RF System Lab, Dec. 25, 2001.
Wellesley Company Sends Body Montiors into Space—Crum, Boston Business Journal, 1998.
www.rfnorkia.com—NORIKA3, printed on Jan. 24, 2002.
Wireless Transmission of a Color Television Moving Image from the Stomach Using a Miniature CCD Camera, Light Source and Microwave Transmitter. Swain CP, Gong F, Mills TN. Gastrointest Endosc 1997;45:AB40.
In Pursuit of the Ultimate Lamp, Craford et al., Scientific American, Feb. 2001.
Manual of Photogrammetry, Thompson (Ed.), Third Edition, vol. Two, Copyright 1944, 1952, 1966 by the American Society of Photogrammetry.
www.jason.net/tinycam.htm, © 2001.
www.middleeasthealthmag.com/article2.htm—Review proves the value of computers, © 2001.
www.pedinc.com Personal electronic devices, © 1997.
BBC News Online—Pill camera to 'broadcast from the gut', Feb. 21, 2000, www.news.bbc.co.uk.
Gonzalez-Correa, et al., Virtual Biopsies in Barrett's Esophagus Using an Impedance Probe, Annals New York Academy of Sciences, vol. 873, Apr. 1999, pp. 313-321.
European Search Report for EP 06 11 1769 dated Sep. 5, 2006.
Office Action dated Aug. 4, 2009, in U.S. Appl. No. 10/481,126.
Office Action, issued Feb. 2, 2010, in U.S. Appl. No. 10/481,126.
International Preliminary Report on Patentability, issued May 6, 2010, for PCT International Application No. PCT/IL2008/001364.
Office Action, issued Jun. 16, 2009, for U.S. Appl. No. 11/280,468.
Final Office Action, issued Dec. 16, 2009, for U.S. Appl. No. 11/280,468.
Office Action, issued Nov. 17, 2005, for U.S. Appl. No. 10/879,054.
Final Office Action, issued May 16, 2006, for U.S. Appl. No. 10/879,054.
Office Action, issued Oct. 4, 2006, for U.S. Appl. No. 10/879,054.
Final Office Action, issued May 18, 2007, for U.S. Appl. No. 10/879,054.
Office Action, issued Jan. 22, 2008, for U.S. Appl. No. 10/879,054.
Final Office Action, issued Aug. 14, 2008, for U.S. Appl. No. 10/879,054.
Office Action, issued Mar. 17, 2009, for U.S. Appl. No. 10/879,054.
Final Office Action, issued Oct. 22, 2009, for U.S. Appl. No. 10/879,054.
Final Office Action, issued Jul. 12, 2010, for U.S. Appl. No. 10/481,126.

* cited by examiner

US 7,833,151 B2

IN VIVO IMAGING DEVICE WITH TWO IMAGERS

PRIOR APPLICATIONS DATA

This application is continuation-in-part of, and claims priority and benefit of, International Patent Application Number PCT/IL2003/001105, filed on Dec. 25, 2003, entitled "In Vivo Imaging Device and Method of Manufacture Thereof", which is incorporated herein by reference in its entirety; which in turn claims priority and benefit of U.S. Provisional Patent Application No. 60/436,004, filed on Dec. 26, 2002, which is incorporated herein by reference in its entirety.

FIELD OF THE INVENTION

The present invention relates generally to in vivo imaging devices, and more specifically to an in-vivo imaging device with a spherical, ellipsoidal, oval, or similar shape.

BACKGROUND OF THE INVENTION

Devices and methods for performing in-vivo imaging of passages or cavities within a body are known in the art. Such devices may include, inter alia, various endoscopic imaging systems and devices for performing imaging in various internal body cavities. Some of these devices use a wireless connection to transmit image data.

Several factors have so far limited the extent to which the size of an imaging device can be reduced. A first factor may be the size of the circuitry connected to the imaging sensor portion of the imaging device. A second factor may be the cumulative widths of the several components of the imaging device. Another factor limiting the size reduction or space usage in imaging devices may be the size of the antenna for transmitting (and/or receiving) data such as image data.

The size of available imaging devices relative to the small openings of many body lumens may be limiting. A reduced size imaging device may provide greater access to body lumens with narrow or restricted points of access. Further, reducing the space taken up by components of imaging devices may allow for other components to be included.

When some in-vivo image devices image lumens that may be relatively large, it may be desirable for the image device to provide a steady image stream of one wall of the lumen. When certain image devices move over the surfaces of such lumens, they may, for example, tumble end over end, thus producing jumpy motion or non-continuous images. Certain image devices may also not provide a relatively steady view of such lumens, and may not easily orient to portions of such lumens that may be desired to be imaged.

SUMMARY OF THE INVENTION

In one embodiment of the present invention an in-vivo imaging device may have an oval, spherical or substantially spherical shape. In another embodiment an imaging device may include a support supporting an image sensor, an illumination source, and an antenna on a first plane of the support and a transmitter and battery support on a second plane of the support. The antenna may be combined with or attached to other elements in the in vivo imaging device so as to possibly reduce the amount of space taken up by it.

BRIEF DESCRIPTION OF THE DRAWINGS

The invention is herein described, by way of example only, with reference to the accompanying drawings, in which like components are designated by like reference numerals, wherein.

Figure 1A:
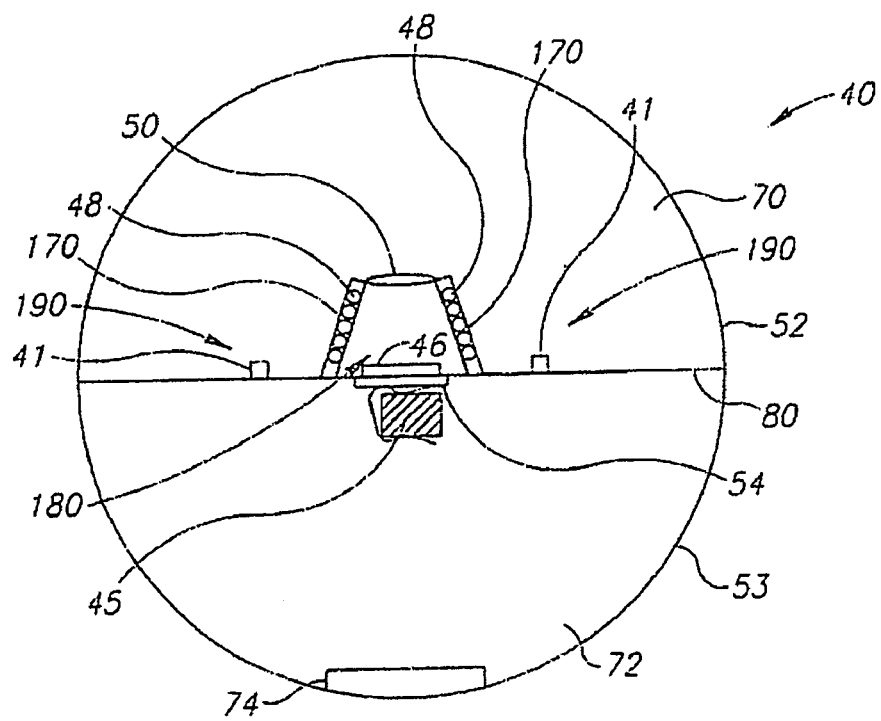
FIG. 1A shows a schematic diagram of an in vivo imaging device according to one embodiment of the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, components and circuits have not been described in detail so as not to obscure the present invention.

One embodiment of the device and system of the present invention may include an imaging device, which may be, for example, a capsule, for example, particularly suited for imaging the stomach or other large lumens (e.g., large intestine), although of course other suitable portions of the body may be imaged. In such applications, for example, high resolution may not be necessary, but there may for example be a need to image a wide field of view. In some embodiments, the entire organ may be imaged for example, to diagnose if a suspected pathology exists; it may be the case that the details of pathology may be less important than its existence. An imaging according to some embodiments device may be used for other suitable purposes besides diagnosing of pathology. Of course, high resolution image devices may be used with embodiments of the present invention, and embodiments of the present invention may be used in other applications. Embodiments of the present invention may allow, for example to reduced size and/or components of an in-vivo image device.

Various embodiments of the present invention may be incorporated into or used with an imaging device similar to some embodiments described in International Application publication number WO 01/65995 entitled "A Device And System For In Vivo Imaging", published on 13 Sep., 2001, which is assigned to the common assignee of the present invention and which is hereby incorporated by reference, and/or embodiments described in U.S. Pat. No. 5,604,531 to Iddan et al., which is assigned to the common assignee of the present invention and which is hereby incorporated by reference in its entirety. In other embodiments, embodiments of the present invention may be incorporated into or used with other imaging capsules or devices, having other structures.

Figure 1B:
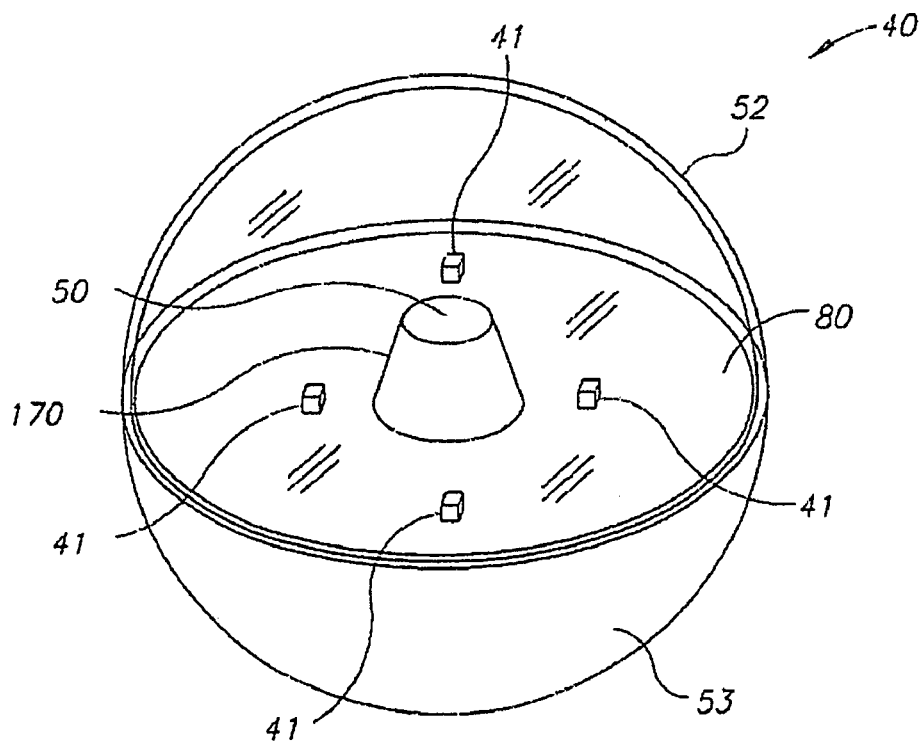
FIG. 1B depicts a perspective view of an in vivo imaging device according to one embodiment of the present invention.

FIG. 1A shows a schematic diagram of an in vivo imaging device according to one embodiment of the present invention. FIG. 1B depicts a perspective view of an in vivo imaging device according to one embodiment of the present invention. Referring to FIGS. 1A and 1B, in an exemplary embodiment, a device 40 may be a swallowable device capturing for example images and other data from within a body lumen, typically the GI tract. Other body lumens may be examined as well by other means other than swallowing, for example insertion with a suitable tool, for example with an endoscope, catheter, implantation, etc. According to one embodiment a generally transparent dome 52 provides a generally transparent cover for the optical elements, provides a sealed barrier to bodily fluids, and may perform other functions (such as holding optical elements). A shell or container 53 may provide a container for components. In one embodiment, the shell or container 53 provides the overall shape for the device; e.g., substantially spherical, etc. Alternately, other components may also provide shape. An upper portion 70 may be separated from a lower portion 72 by, for example, a support 80; in an alternate embodiment such a separation may not be performed. When used herein, upper and lower are relative terms, to be used interchangeably as per the context. The portions may not evenly split the device. The shell or container may be uniform, or may have multiple components For example, a portion of the shell may be a clear optical window or dome, or the shell may be manufactured from multiple components.

Typically, the outer shape of the device 40 (which in the embodiment shown is formed by dome 52 and shell 53, but may be formed by other components) may be ellipsoidal, spherical or substantially spherical. When used herein, "spherical or substantially spherical" may be defined as a geometrical shape having a diameter r and a longitudinal axis L wherein $r<=L<=1.5r$. When $L=1.5r$, the shape may be an ellipsoid, and also may be considered to be oval shaped. In one embodiment r may be about 11.4 mm; however, other dimensions may be used. Note that, as device 40 may be rotated about an axis, different cross sections of the device 40 may differ—e.g., the device 40 may be a somewhat irregular sphere or ellipsoid. The shape of the device 40 may differ when viewed from different angles.

Typically, device 40 may include at least one sensor such as an image sensor 46, for capturing images (and possibly other sensors, such as a temperature sensor, a pH sensor, a pressure sensor, etc.). A set of illumination source(s) 41 (where set can include one item) such as, for example, a set of LEDs, such as for example white LEDs (other suitable elements may be used) may be used to illuminate an area for viewing.

An optical system, may include, for example, one or more optical elements, such as one or more lenses or composite lens assemblies 50, one or more suitable optical filters (not shown), or any other suitable optical elements (not shown), may aid in focusing reflected light onto the image sensor 46 and performing other light processing. The lens 50 may be mounted on an optical isolation element 170. Isolation element 170 may aid in partially or completely optically isolating sections of the device from each other, for example by preventing light from illumination sources from reaching imaging systems directly, as opposed to via reflecting off of imaged objects. Other systems or methods for positioning the lens(es) may be used. In one embodiment, the field of view may be 80-90 degrees; other suitable fields of view may be used, such as a field of view of 140 degrees, or other suitable fields of view, such as a field of view in the range of between 80-140 degrees. The focus distance may typically be between 0 to 40 mm; however, other suitable distances may be used.

Device 40 may, for example, have components similar to components in embodiments described in U.S. Pat. No. 5,604,531 and/or WO 01/65995, described above. However, device 40 may be any sort of in-vivo sensor device and may have other components and configurations. For example, device 40 or components of device 40 may be included in an endoscope.

Device 40 typically may include a transmitter 54, for transmitting image and other (e.g., non-image) information to a receiving device, and may include other components, such as, for example, a compression module (not shown), for compressing data. The transmitter 54 may typically be an ultra low power radio frequency (RF) transmitter with high bandwidth input, possibly provided in chip scale packaging. The transmitter 54 may also include circuitry and functionality for controlling the device 40. Transmitter 54 may be, for example, an ASIC, "computer on a chip", microcontroller, etc., or other component. Transmitter 54 may be in one embodiment a generalized integrated device that may include, for example, transmitter and/or receiver capability, a controller, drivers for the illumination devices, and possibly a variety of analog and/or digital elements. According to some embodiments of the present invention, antenna 48 and/or transmitter 54 may be used for receiving data, for example from an external system such as an external receiving and display system.

Components such as image sensor 46, illumination source (s) 41, optical isolation element 170, and transmitter 54 may be mounted on the support 80, which may be, for example, a circuit board e.g. a Printed Circuit Board (PCB) or plastic board or sheet. According to one embodiment of the present invention, the circuit board may include rigid and flexible portions. According to some embodiments of the present invention, each rigid portion of the circuit board may be connected to another rigid portion of the circuit board by a flexible connector portion of the circuit board. According to one embodiment of the present invention, each rigid portion of the circuit board may include two rigid sections; sandwiched between the rigid sections is a flexible connector portion of the circuit board for connecting the rigid boards. In alternate embodiments, other arrangements of components may be placed on a circuit board having rigid portions connected by flexible portions. According to some embodiments of the present invention, Support 80 may be another structure or substrate, and may be made of other substances, and components need not be mounted on a separate support.

In alternate embodiments, a circuit board having rigid portions and flexible portions may be used to arrange and hold components in other in vivo sensing devices, such as a swallowable capsule measuring pH, temperature or pressure, or in a swallowable imaging capsule having components other than those described above. Such circuit boards may be similar to embodiments described in U.S. application Ser. No. 10/879,054 entitled IN VIVO DEVICE WITH FLEXIBLE CIRCUIT BOARD AND METHOD FOR ASSEMBLY THEREOF, and U.S. application No. 60/298,387 entitled IN VIVO SENSING DEVICE WITH A CIRCUIT BOARD HAVING RIGID SECTIONS AND FLEXIBLE SECTIONS, each incorporated by reference herein in their entirety.

Figure 2A:
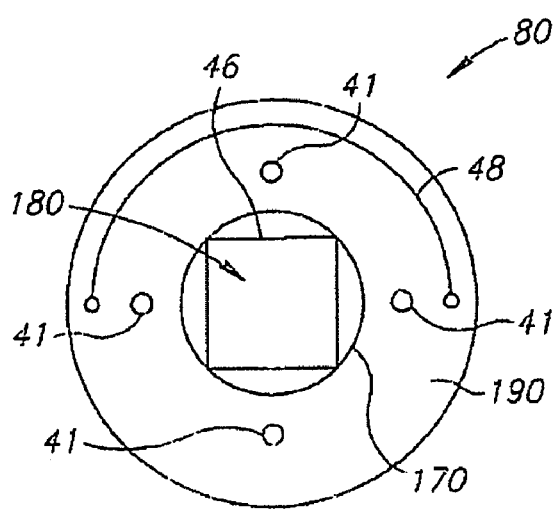
FIG. 2A depicts a top view of a support of an imaging device, according to an embodiment of the present invention.
Figure 2B:
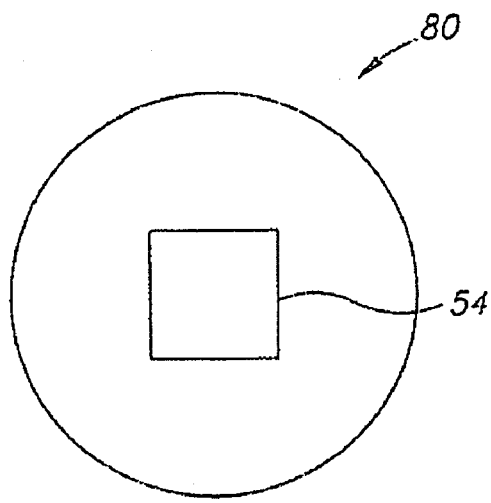
FIG. 2B depicts a bottom view of a support of an imaging device, according to an embodiment of the present invention.

In one embodiment image sensor 46, illumination source (s) 41 and transmitter 54 and/or other components may be mounted on the support 80 so as to minimize the amount of space taken up by such components. FIG. 2A depicts a top view of a support of an imaging device, according to an embodiment of the present invention. FIG. 2B depicts a bottom view of a support of an imaging device, according to an embodiment of the present invention. When used herein, top and bottom are relative terms, and may be interchangeable depending on the context.

Figure 7A:
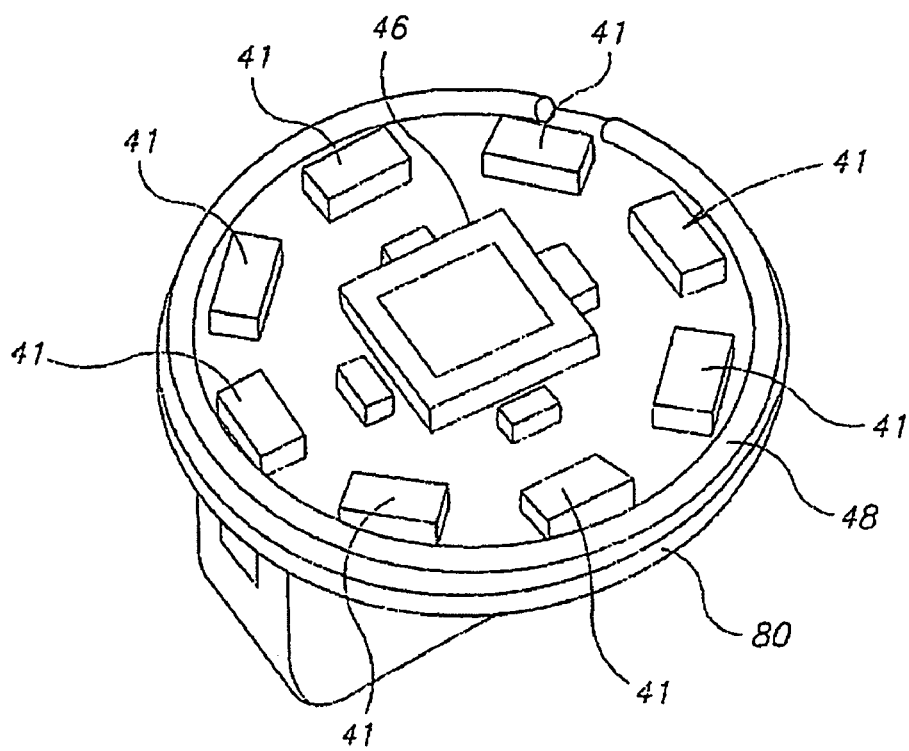
FIG. 7A depicts a top view of a support of an imaging device, according to an embodiment of the present invention.
Figure 7B:
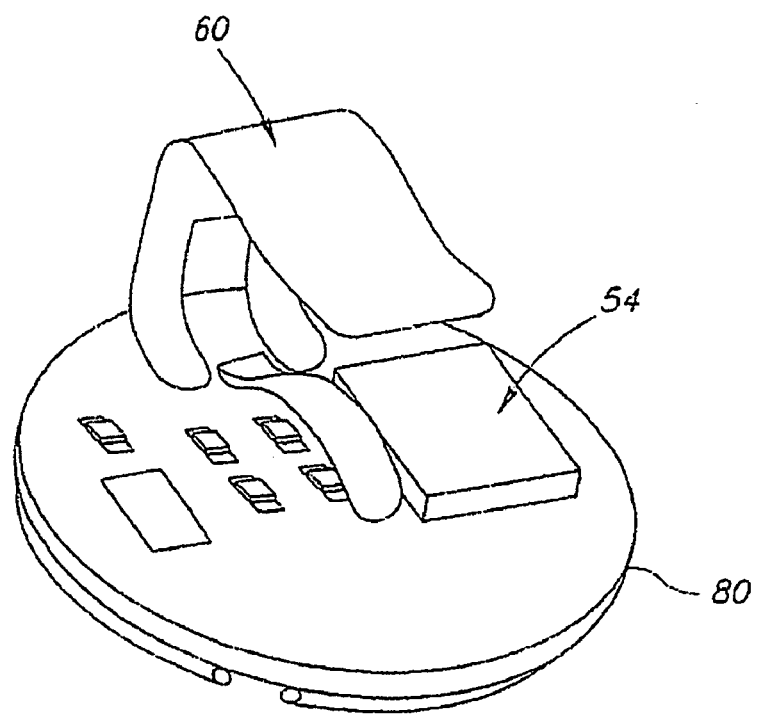
FIG. 7B depicts a bottom view of a support of an imaging device, according to an embodiment of the present invention.

FIGS. 7A and 7B depicts an alternate view of support 80, according to an embodiment of the present invention. Referring to FIGS. 7A and 7B, support 80 may have mounted on it on one face an image sensor 46, one or more illumination source(s) 41, antenna 48, and possibly other components, such as optical isolation element 170 (shown in FIGS. 1A and 1B). The embodiment shown in FIG. 7A depicts 8 illumination sources. Other suitable numbers of illumination sources may be used. Support 80 has mounted on it on another face transmitter 54, a battery support 60, for holding power source (s) 45 (which in one embodiment may be batteries), and possibly other components. In other embodiments, the battery support may be any component providing battery contact so as to provide power to one or more components in device 40. Other sets of components may be included on the various faces or sides of a support or substrate.

Referring again to FIG. 1A, image sensor 46, one or more illumination source(s) 41, and an antenna 48 (through which the transmitter 54 may transmit) may be placed on the top side or face of the support, and transmitter 54 on the bottom side or face of the support 80. The various components may communicate electrically, for example, through wires or electrical contacts (not shown) on support 80 that may cross from one side of the support 80 to the other by holes or vias.

Various components of the device 40, and other components, may be placed on the support 80 in different manners. For example, the transmitter 54 and illumination source(s) 41 may be placed on the same side. The one or more illumination source(s) 41 may be arranged in different manners. In an alternate embodiment, the various components of the device 40 need not be mounted or configured on a support or circuit board as shown herein.

In one embodiment of the present invention, sections of an imaging device may be optically isolated from one another. One or more optical isolation elements 170 may be used to optically isolate sections of the device, for example to keep light scatter from illumination source(s) 41 from reaching image sensor 46 and to separate an image sensor section 180 from one or more illumination section(s) 190.

Generally, an illumination section includes the area including at least illumination elements and an imaging section includes areas including at least one or more image devices. However, an illumination section may include other additional components and areas, and an imaging section may include other additional components and areas. Further, each of an illumination section and imaging section may be divided into two or more non-contiguous sections, and may have different configurations than shown. The illumination portion may include suitable illumination sources such as LEDs or white LEDs; other illumination sources may be used.

In certain embodiments, the antenna 48 may be configured to take up a minimum of space within the device 40. For example, the antenna 48 may be combined with, embedded within, substantially within, or attached to other elements, such as a support, so as to not take up a large amount of space. The antenna 48 may also be surrounded by or nestled within components such as a support, separation or isolation element, etc.

Figure 3A:
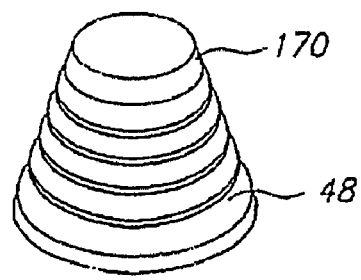
FIGS. 3A, 3B and 3C depict an optical isolation element and antenna according to one embodiment of the present invention.
Figure 3B:
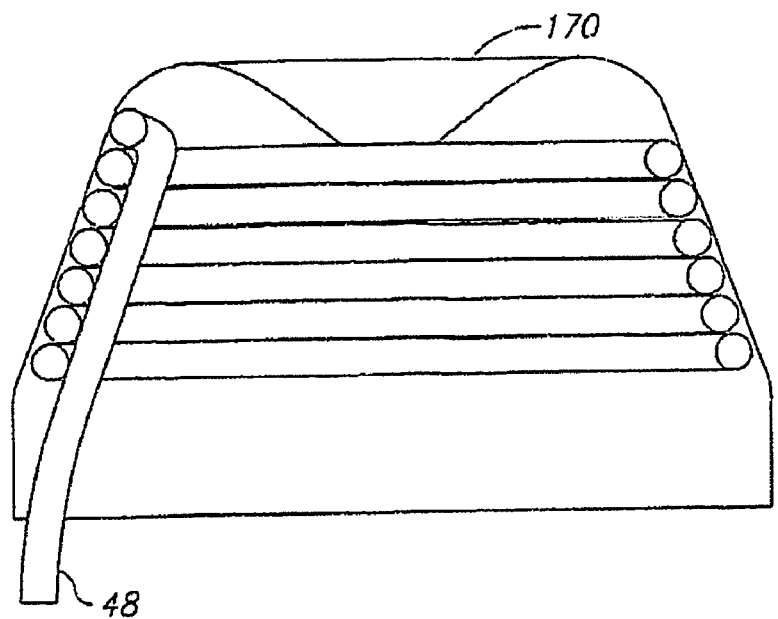
Figure 3C:
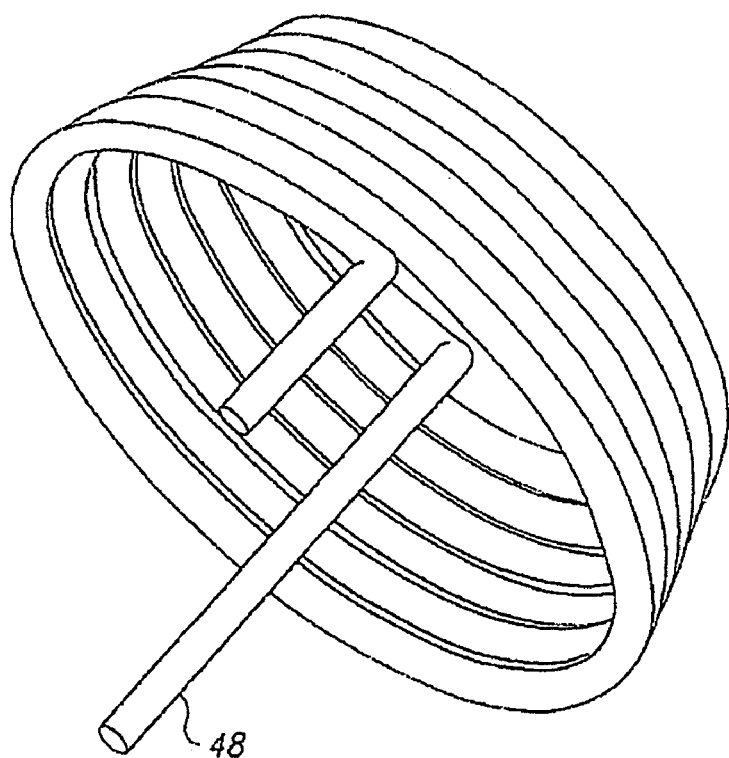

In one embodiment, antenna 48 may be placed within or mounted on a surface of the optical isolation element 170. In the embodiment shown in FIG. 1A, antenna 48 may be coiled within or embedded within or substantially within (a portion may extend outside) isolation element 170, for example by being placed between two sections of isolation element 170 or by being molded or embedded within the isolation element 170. FIG. 3A depicts optical isolation element 170 and antenna 48 according to one embodiment. FIG. 3B is a cut-away view depicting optical isolation element 170 and antenna 48 according to one embodiment. FIG. 3C depicts antenna 48 according to one embodiment. Referring to FIG. 3A, optical isolation element 170 may be in one embodiment a cone, and antenna 48 may be wrapped around the outside of optical isolation element 170. Referring to FIG. 3b, antenna 48 may be coiled on the inside of isolation element 170. Antenna 48 need not be placed within or on the isolation element 170, and the isolation element 170 need not be included. Optical isolation element 170 may be of other suitable shapes (e.g., FIG. 5). In alternate embodiments, other suitable numbers of optical isolation elements may be used, having different forms. The optical isolation elements may be, for example, extensions of components of the device, such as the illumination sources or image sensor, a piece integrated into or extending from the dome or lens, a translucent or semi-transparent member, or other suitable forms.

In another embodiment, antenna 48 may be mounted on the support 80. For example, the antenna 48 may be mounted in a flat manner over the surface of support 80 (FIG. 2A). In FIG. 2A, antenna 48 may be arranged around the periphery of the support 80. Alternately, antenna 48 may be arranged in a different manner or pattern on support 80. For example, antenna 48 may be embedded within or substantially within the support 80.

The transmitter 54 may be connected to antenna 48 by, for example, wires, or connections (not shown) on the support 80 or through the support 80 (in the case, for example that the antenna 48 and transmitter 54 may be on opposite sides of the support 80). In alternate embodiments, the antenna may not be configured to take up a small amount of space.

Referring again to FIG. 1A, typically, the device includes a power source 45, such as one or more batteries. For example, the power source 45 may include silver oxide batteries, lithium batteries, or other electrochemical cells having a high energy density, or the like. Other suitable power sources may be used. Power induction from an external source may be used.

In one embodiment, the location of the center of gravity ("c.g.") vis-à-vis the geometric center of the device 40 may be of importance for the stabilization of the optical axis of the device 40 as it enters cavities larger then it's own size. One or more weight(s) or ballast(s) 74 may be included at one portion of the device 40, for example at the bottom of the lower portion 72 (bottom and top being relative terms, interchangeable as per the context). Weight 74 may be included at other portions of the device 40. A weight or ballast may take the form of other functional components of the device—for example, a battery may be positioned to alter the weight or mass balance of the device. Counterweight or other elements that may decrease the specific gravity may be included—for example, a gas may be included at a portion of the device to alter the specific gravity or weight distribution. Weight 74 may be arranged so that device 40 holds, substantially, one orientation during its traverse of the GI tract, or tends to return to such orientation when moved from that orientation. The center of gravity may be typically opposite to the direction of view. In other embodiments, a weight may be included at one portion of device 40, to for example counter balance existing weights, and for example place the center of gravity in for example, the geometrical center of device 40. In one embodiment of the present invention, device 40 may be configured not to hold a specific orientation.

Other components and sets of components may be used. For example, the power source may be an external power source transmitting power to the device, and a controller separate from the transmitter 54 may be used.

In one embodiment, the image sensor 46 may be a complementary metal oxide semiconductor (CMOS) image sensor. The CMOS image sensor may be typically an ultra low power image sensor and may be provided in chip scale packaging (CSP). One suitable CMOS camera may be, for example, a "camera on a chip" CMOS image sensor. Other types of CMOS image sensors may be used. In another embodiment, other suitable image sensors may be used, such as for example, a CCD image sensor, or other suitable image sensors. Typically, the image sensor may be square in shape (e.g., a 256×256 CMOS array). Other dimensions, for example 512×512 elements, may be used. Other shapes, such as for example rectangular shapes, or other suitable shapes may be used.

In vivo image device 40 may transmit image or other information to a receiver system and the images and other information may be displayed on a display system. In one embodiment, a reception and display system such as those described in embodiments in the above mentioned WO 01/65995 and/or U.S. Pat. No. 5,604,531 may be used; in alternate embodiments, other reception or display systems, having other configurations, may be used.

Figure 4:
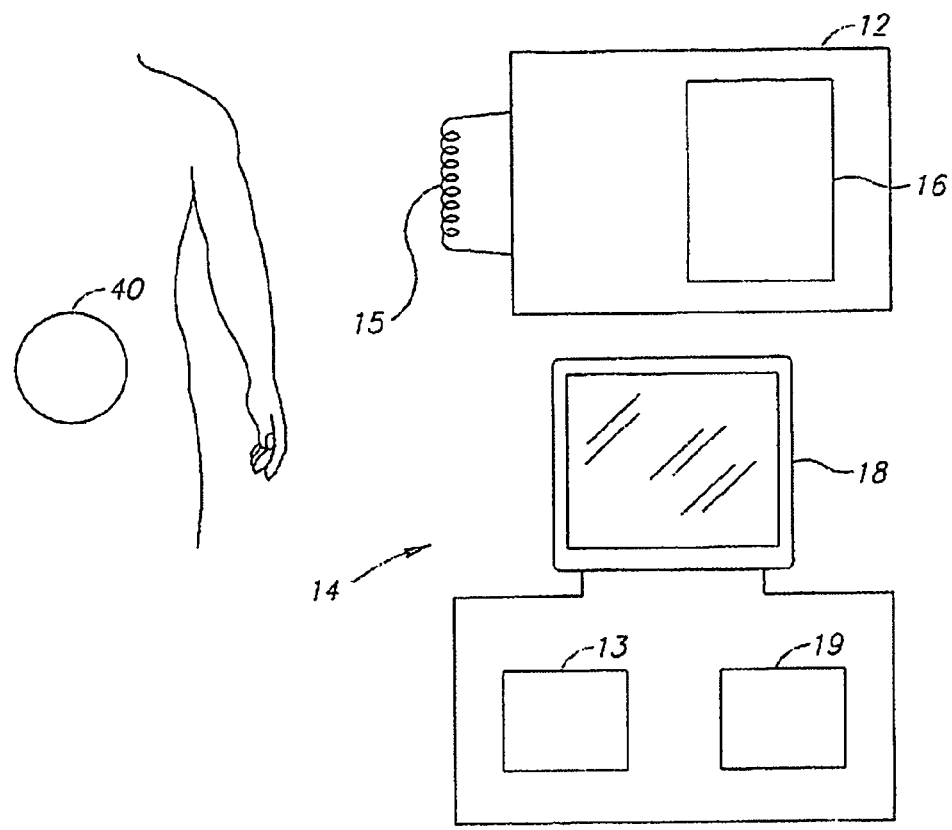
FIG. 4 depicts elements of an imaging system according to one embodiment of the present invention.

FIG. 4 depicts elements of an imaging system according to one embodiment of the present invention Referring to FIG. 4, preferably, located outside the patient's body in one or more locations, may be a receiver 12, preferably including an antenna or antenna array 15, for receiving image and possibly other data from device 40, a receiver storage unit 16, for storing image and other data, a data processor 14, a data processor storage unit 19, and an image monitor 18, for displaying, inter alia, the images transmitted by the device 40 and recorded by the receiver 12. Typically, the receiver 12 and receiver storage unit 16 may be small and portable, and may be worn on the patient's body during recording of the images. Typically, data processor 14, data processor storage unit 19 and monitor 18 may be part of a personal computer or workstation, which may include standard components such as a processor 13, a memory (e.g., storage 19, or other memory), a disk drive (not shown), and input-output devices (not shown), although alternate configurations may be possible.

In alternate embodiments, the data reception and storage components may be of another configuration. It should be emphasized that other embodiments may include a wired rather than wireless device. In such a case, certain elements shown in FIG. 1A and FIG. 4 may be omitted, such as transmitter 54, antenna 48, antenna array 15 and receiver 12.

Typically, the device 40 may be swallowed by a patient and for example traverses the patient's GI tract, however, other body lumens or cavities may be imaged or examined, and the device need not be swallowable. Typically, the device 40 may transmit information (e.g., image information) in discrete portions. Each portion may for example, typically corresponds to an image or frame. Other suitable transmission methods may possible. For example, the device 40 may capture image or other information once every half second, and, after capturing such an image, may for example transmit the information to the receiving antenna. Other capture rates may be possible. Typically, the image data recorded and transmitted may be digital color image data, although in alternate embodiments other image formats (e.g., black and white image data) may be used. In one embodiment, each frame of image data may include 256 rows of 256 pixels each, each pixel including data for color and brightness, according to known methods. For example, in each pixel, color may be represented by a mosaic of four sub-pixels, each sub-pixel corresponding to primaries such as red, green, or blue (where one primary may be represented twice). The brightness of the overall pixel may be recorded by, for example, a one byte (i.e., 0-255) brightness value. Other data formats may be used, and other image formats may be used.

Figure 5A:
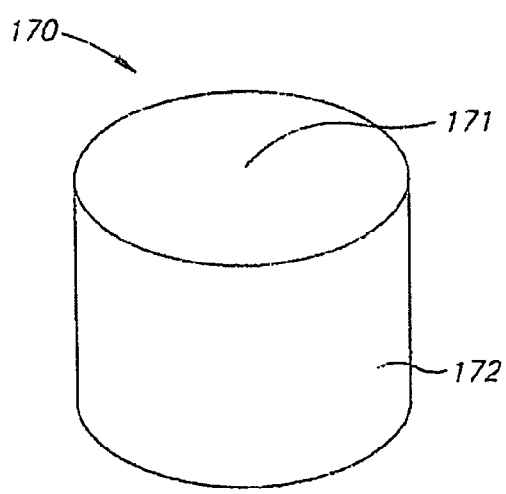
FIG. 5A is a side view of an optical isolation element according to one embodiment of the present invention.
Figure 5B:
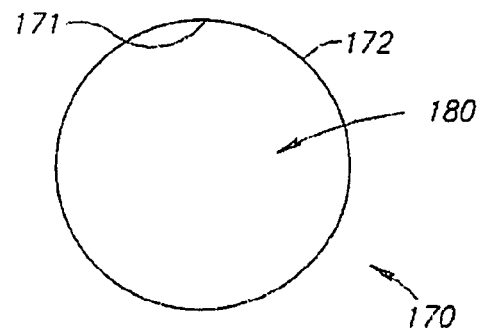
FIG. 5B is a top view of an optical isolation element according to one embodiment of the present invention.

FIG. 5A is a side view of an optical isolation element according to one embodiment of the present invention. FIG. 5B is a top view of an optical isolation element according to one embodiment of the present invention. Referring now to FIGS. 5A and 5B, optical isolation element 170 may be one relatively flat ring or cone of plastic, polymer, or other suitable material. For example, ABS (acrylonitrile butadiene styrene) may be used. The isolation element 170 may be of other forms, for example the cone of FIG. 3, may be made from other suitable materials (including more than one material) and may be constructed from multiple pieces. An antenna (FIG. 1A) may be included in or on isolation element 170. For example, an antenna may be molded within the material of isolation element 170) or mounted on a surface (e.g., inner surface 171 or outer surface 172) of isolation element 170.

In FIG. 1A isolation element 170 is shown for example as a single ring shown in cross section, but may have other suitable forms. The optical isolation element(s) 170 may be, for example, an opaque or translucent barrier, a light trap, an optical filter, a series of separate barriers, or any other suitable structure.

Isolation element 170 may be mounted in the device 40 by, for example, gluing, acoustic welding, friction fit, being held by other assembled components, or by other methods. Isolation element 170 may be part of or an extension of other elements, such as a supporting surface such as for example support 80. Isolation element 170 may, for example, separate an illumination section 190 and an imaging section 180, which in FIG. 1A, for example, may be generally located within the illumination section 190. In the embodiment depicted, the imaging section 180 may be round, and the illumination section 190 may be ring shaped or substantially ring shaped.

Embodiments of the device may be typically autonomous and typically self-contained. For example, the device may be a capsule or other units where all the components are substantially contained within a container or shell, and where the device does not require any wires or cables to, for example, receive power or transmit information. The device may communicate with an external receiving and display system to provide display of data, control, or other functions. For example, power may be provided by an internal battery or a wireless receiving system. Other embodiments may have other configurations and capabilities. For example, components may be distributed over multiple sites or units. Control information may be received from an external source.

In one embodiment, the imaging device may be spherical or substantially spherical (which when used herein includes an ellipsoidal shape). Such a shape may enable the device to glide or roll over the typically moist surface of body lumens such as the stomach. Also, a spherically shaped device may glide or roll over the ridges formed on GI tract lumen walls (such as the stomach wall) rather than get stuck in or on these ridges. In such a case, the motion of the image sensor within the device may be relatively smooth and continuous. This may be in contrast to devices of other shapes (erg., oblong shapes) that may produce jumpy motion and non-continuous images in the same context when for example tumbling over surfaces.

An optional ballast or weight may allow one portion, such as the image sensor 46, to be usually oriented upwards. In such an embodiment, the images captured may tend to be not of the wall on which the device may be resting, in the case that the device may be resting on a surface in a lumen, but rather may include a view oriented outward from the wall. In a lumen that may be relatively large (e.g., the stomach or large intestine), when the patient may be oriented so gravity acts on the ballast or weight in a certain manner, the wall opposite the wall on which the device may be resting is imaged, rather than a wall close to the device which may block the view of the image device. Such an embodiment may provide a relatively steady view of a lumen, and be easily oriented to portions of such lumens that may be desired to be imaged.

Figure 6:
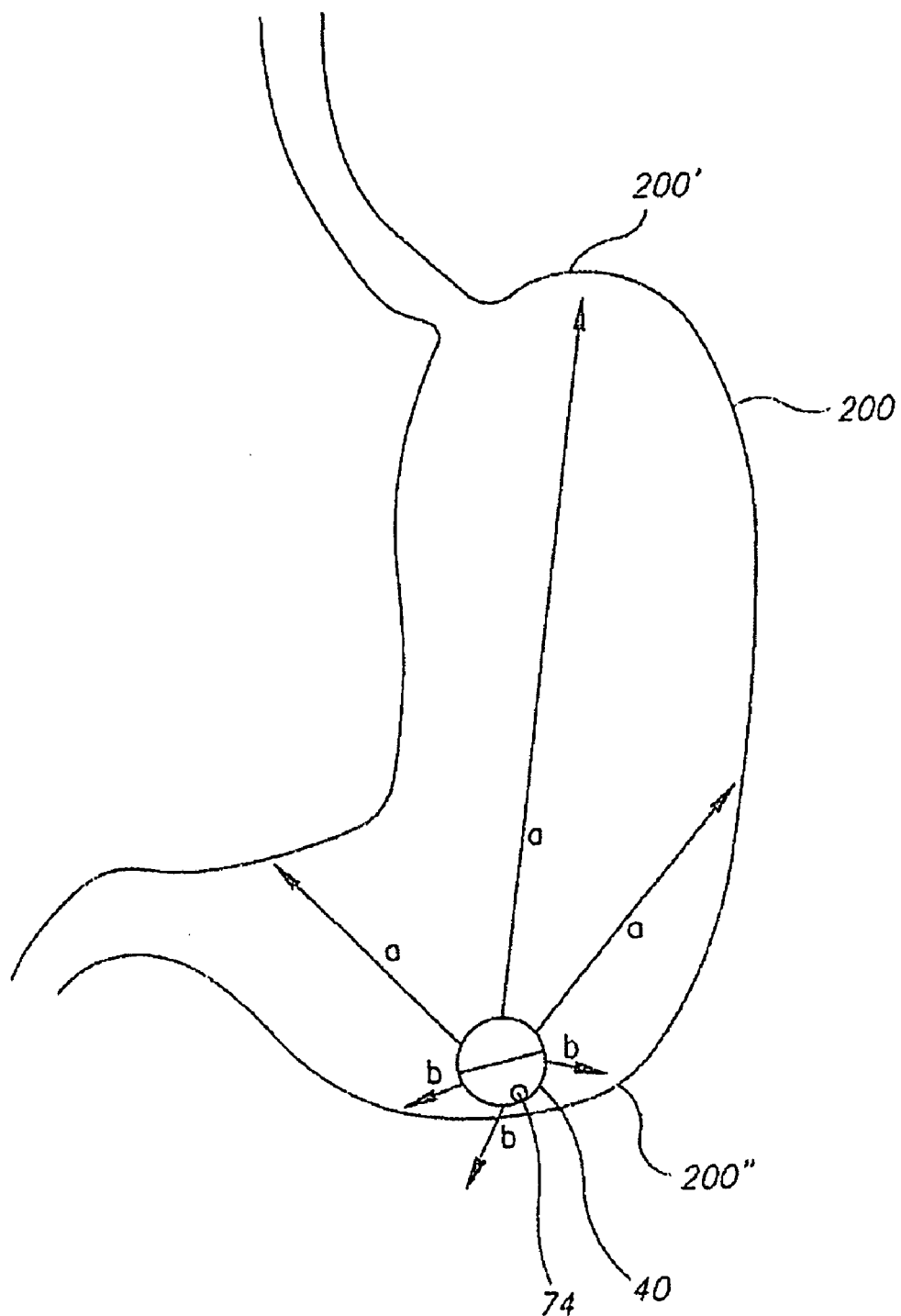
FIG. 6 depicts the device in a patient's stomach according to one embodiment of the present invention.

FIG. 6 depicts the device 40 in a patient's stomach 200 according to one embodiment of the present invention. Referring to FIG. 6, if weight or ballast 74 may be included in device 40, the device 40 may tend to be oriented so that the image sensor 46 (FIG. 1A) may be oriented generally upwards. Thus, assuming the stomach 200 may be oriented so that the top 200' may be above the bottom 200", the image sensor 46 may capture images in, for example, directions marked as a, and does not generally capture images in directions marked as b.

In embodiments where the device images one wall of a lumen from a "far wall", that illumination sources typically output enough light so that the far wall may be adequately illuminated Various methods of altering the amount of light output by the illumination units, for example, in response to detection of the amount of light required or the amount of light received by the image device, may be used. Embodiments of devices and methods for altering the light output from an image device are described in International Application PCT/IL02/00622 filed 26 Jul. 2002, assigned to the assignee of the present invention, incorporated herein by reference in its entirety. An antenna as described herein in various embodiments need not be used in a device having for example, a substantially spherical or a certain shape. For example, such antennas may be used in oblong shaped devices. Similarly, a circuit board or series of circuit boards as described herein in various embodiments need not be used in a device having a substantially spherical or a certain shape. For example, such configurations may be used in oblong shaped devices. Furthermore, an imaging device according to an embodiment of the invention having a spherical or substantially spherical shape need not include an antenna as described herein or a circuit board or internal configuration as described herein.

According to some embodiments of the invention there is provided a method of manufacturing a substantially spherical in vivo imaging device According to one embodiment the method may include the steps of mounting an image sensor and a transmitter on a single support and encapsulating the support in a substantially spherical housing. According to some embodiments an image sensor and a transmitter may be mounted on two faces of the support, typically, opposing faces. The support and/or housing according to embodiments of the invention may be, for example, as described above.

Figure 8:
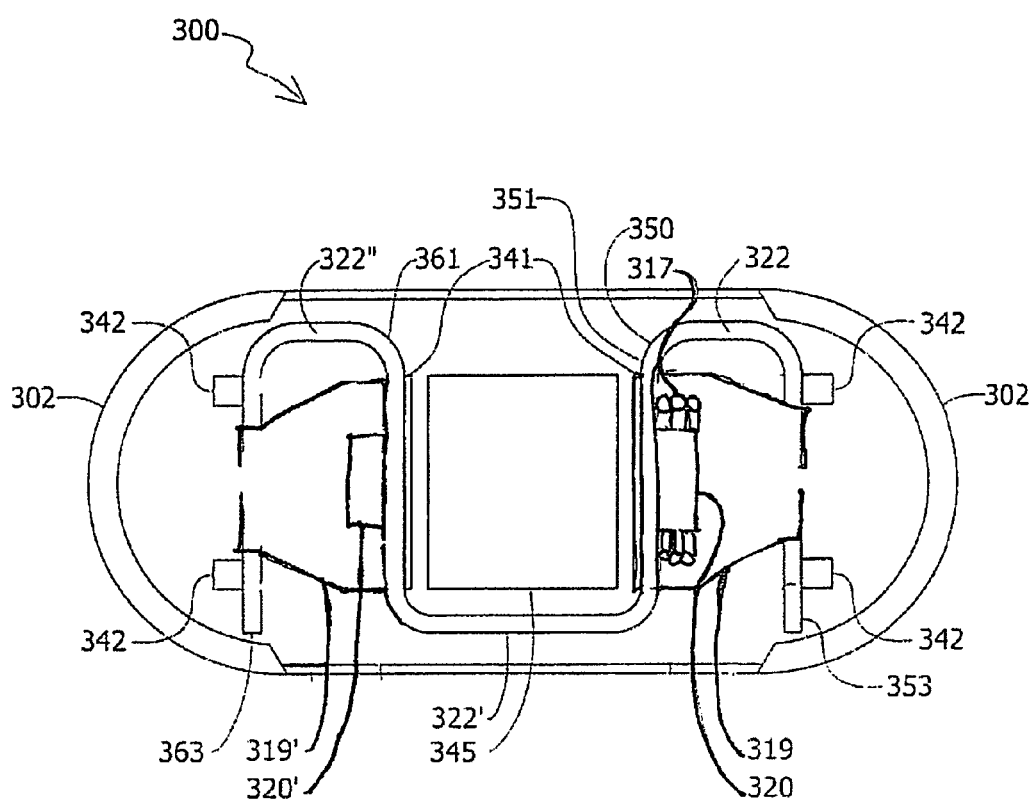
FIG. 8 schematically illustrates an in vivo imaging device according to another embodiment of the invention.

Another embodiment of the invention is schematically illustrated in FIG. 8, in which a longitudinal cross section, of device 300 is schematically shown. According to one embodiment of the present invention, device 300 may include two optical domes 302 behind which are situated illumination sources 342, two lens holder 319 and 319', two imagers 320 and 320' a transmitter such as an ASIC and a processor. The device 300 may further include a power source 345, which may provide power to the entirety of electrical elements of the device and an antenna 317 for transmitting video signals from the imagers 320 and 320'. According to some embodiments of the present invention, the antenna 317 may be combined with, embedded within, substantially within, or attached to elements, such as a support e.g. the lens holder 319 so as to not take up a large amount of space. The antenna 317 may also be surrounded by or nestled within components such as a support, separation or isolation elements, etc. According to some embodiments of the present invention, device 300 is capable of simultaneously obtaining images of the body lumen, for example, the GI tract, from two ends of the device. For example, device 300 may be a cylindrical capsule having a front end and a rear end, which is capable of passing the entire GI tract. The system in a cylindrical capsule can image the GI tract in the front and in the rear of the capsule.

According to one embodiment of the present invention, the various components of the device 300 may be disposed on a circuit board 350 including rigid and flexible portions; preferably the components are arranged in a stacked vertical fashion For example, rigid portion 351 of the circuit board 350 may hold a transmitter, an imager 320 and a lens holder 319 and an antenna 317, while rigid portion 361 may hold a processor, an imager 320' and a lens holder 319'; the other side of the rigid portions 351 and 361 may include, for example, a contact 341 for battery or power source 345. According to one embodiment of the present invention, rigid portions 353 and 363 of the circuit board 350 may include, for example, an illumination source, such as one or more LEDs 342 or other illumination sources. According to some embodiments of the present invention, each rigid portion of the circuit board may be connected to another rigid portion of the circuit board by a flexible connector portion (e.g. 322 322' and 322") of the circuit board 350. According to one embodiment of the present invention, each rigid portion of the circuit board may include two rigid sections; sandwiched between the rigid sections is a flexible connector portion of the circuit board for connecting the rigid boards. In alternate embodiments, other arrangements of components may be placed on a circuit board having rigid portions connected by flexible portions.

One embodiment of the invention includes a method of manufacturing an in vivo imaging device, the method including mounting an antenna on a rigid section of a circuit board having a plurality of rigid sections and a plurality of flexible sections, and folding the circuit board into an in-vivo imaging device housing. One embodiment includes folding the circuit board such that the rigid sections of the circuit board are stacked vertically. One embodiment includes mounting an antenna on a first plane of the rigid section and mounting a transmitter on a second plane. One embodiment includes mounting an antenna on a first plane of the rigid section and mounting a battery support on a second plane.

Figure 9:
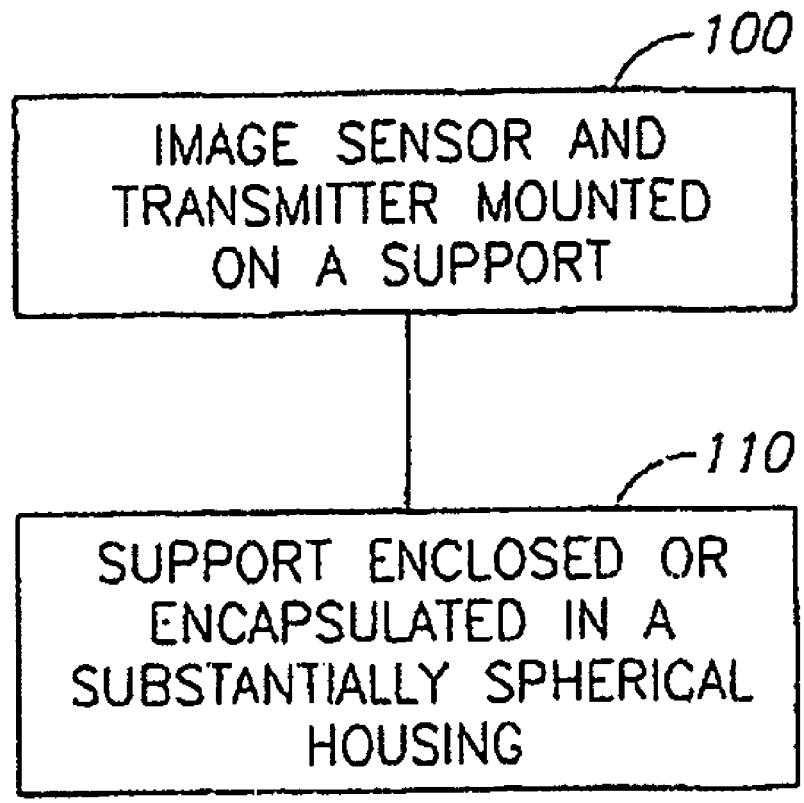
FIG. 9 depicts a set of steps of a method for manufacture of an imaging device, according to one embodiment of the invention.

FIG. 9 depicts a set of steps of a method for manufacture of an imaging device, according to one embodiment of the invention. Referring to FIG. 9, in step 100, an image sensor and a transmitter are mounted on a support, for example on a circuit board e.g. a circuit board including rigid and flexible portions. In alternate embodiments, additional components may be mounted on the support, and the configuration of the various components may vary. For example, an antenna may be mounted on the support, possibly on a face or side different from the transmitter. In further embodiments, other component configurations may be achieved; for example, an image sensor and transmitter need not be mounted on the same support.

In step 110, the support may be enclosed or encapsulating in a substantially spherical housing. Other components may be included; for example a ballast or other weight may be included within housing.

Other steps or series of steps may be used.

While the invention has been described with respect to a limited number of embodiments, it will be appreciated that many variations, modifications and other applications of the invention may be made which are within the scope and spirit of the invention.

The invention claimed is:

1. A cylindrical swallowable in vivo imaging device comprising:
   a first dome-shaped end and a second dome-shaped end, each dome-shaped end at an opposite end of the device;
   a first imager imaging via the first dome-shaped end;
   a first power contact and a second power contact for a power source to provide power to device components;
   a first illumination source illuminating via the first dome-shaped end;
   a second imager imaging via the second dome-shaped end;
   a second illumination source illuminating via the second dome-shaped end;
   a circuit board comprising a plurality of rigid circuit board sections connected by a plurality of flexible circuit board sections, the first imager and first power contact disposed on opposite sides of a first of the plurality of rigid circuit board sections and the second imager and second power contact disposed on opposite sides of a second of the plurality of rigid circuit board sections.

2. The in vivo imaging device according to claim 1, comprising an antenna mounted on a rigid circuit board section, wherein the antenna is a single ring or a coil.

3. The in vivo imaging device according to claim 1, comprising an antenna wherein the antenna is mounted on the periphery of a rigid circuit board section.

4. The in vivo imaging device according to claim 1, comprising an isolation element.

5. The in vivo imaging device according to claim 4, wherein the isolation element is selected from a group consisting of: an opaque barrier, a translucent barrier, a light trap, and an optical filter.

6. The in vivo imaging device according to claim 4 wherein the isolation element is attached to a component of said in vivo imaging device.

7. The in vivo imaging device according to claim 4, wherein the isolation element is a lens holder.

8. The in vivo imaging device according to claim 4, wherein the isolation element supports an optical system.

9. The in vivo imaging device according to claim 4, comprising an antenna embedded within said isolation element.

10. The in vivo imaging device according to claim 9, comprising an antenna coiled within said isolation element.

11. The in vivo imaging device according to claim 4, comprising an antenna wrapped around the isolation element.

12. The in vivo imaging device according to claim 1 wherein the device is autonomous.

13. A cylindrical swallowable in vivo imaging device comprising:
   a first dome-shaped end and a second dome-shaped end, each dome-shaped end at an opposite end of the device;
   a first imager imaging via the first dome-shaped end;
   a first power contact and a second power contact for a power source to provide power to device components;
   a first illumination source illuminating via the first dome-shaped end;
   a second imager imaging via the second dome-shaped end;
   a second illumination source illuminating via the second dome-shaped end;
   a circuit board comprising a plurality of rigid circuit board sections connected by a plurality of flexible circuit board sections; and
   an antenna and a transmitter disposed on opposite sides of one of said plurality of rigid circuit board sections,
   the first imager and first power contact disposed on opposite sides of a first of said plurality of rigid circuit board sections, and the second imager and second power contact disposed on opposite sides of a second of said plurality of rigid circuit board sections.

14. The in vivo imaging device according to claim 13, wherein the antenna is selected from a group consisting of: a single ring and a coil.

15. The in vivo imaging device according to claim 13, wherein the antenna is mounted around the periphery of the rigid circuit board section on which it is mounted.

* * * * *